US011026777B2

(12) United States Patent
Hall et al.

(10) Patent No.: US 11,026,777 B2
(45) Date of Patent: Jun. 8, 2021

(54) LAYERED MEDICAL APPLIANCES AND METHODS

(71) Applicant: Merit Medical Systems, Inc., South Jordan, UT (US)

(72) Inventors: John Hall, North Salt Lake, UT (US); Wayne Mower, Bountiful, UT (US); Rachel Simmons, Bountiful, UT (US); Bart Dolmatch, Palo Alto, CA (US)

(73) Assignee: Merit Medical Systems, Inc., South Jordan, UT (US)

( * ) Notice: Subject to any disclaimer, the term of this patent is extended or adjusted under 35 U.S.C. 154(b) by 82 days.

(21) Appl. No.: 16/035,334

(22) Filed: Jul. 13, 2018

(65) Prior Publication Data

US 2019/0008665 A1  Jan. 10, 2019

Related U.S. Application Data

(63) Continuation of application No. 15/053,232, filed on Feb. 25, 2016, now Pat. No. 10,028,852.
(Continued)

(51) Int. Cl.
*A61F 2/07* (2013.01)
*A61L 27/50* (2006.01)
(Continued)

(52) U.S. Cl.
CPC ............... *A61F 2/07* (2013.01); *A61F 2/915* (2013.01); *A61L 27/18* (2013.01); *A61L 27/507* (2013.01); *A61L 31/06* (2013.01); *A61F 2002/072* (2013.01); *A61F 2210/0014* (2013.01); *A61F 2210/0076* (2013.01); *A61F 2220/005* (2013.01); *A61F 2250/0018* (2013.01); *A61F 2250/0023* (2013.01); *A61F 2250/0028* (2013.01); *A61F 2250/0051* (2013.01);
(Continued)

(58) Field of Classification Search
CPC . A61F 2/04–2002/07; A61F 2250/0023–0024; A61F 2250/0051; A61F 2210/0076
See application file for complete search history.

(56) References Cited

U.S. PATENT DOCUMENTS 3,203,365 A  8/1965  Bowe et al.
4,043,331 A  8/1977  Martin et al.
(Continued)

FOREIGN PATENT DOCUMENTS

AT  366546  6/1976
CN  1823687  8/2006
(Continued)

OTHER PUBLICATIONS

EP Examination Report dated May 28, 2019 for EP12755426.9.
(Continued)

*Primary Examiner* — Rebecca S Preston
(74) *Attorney, Agent, or Firm* — Stoel Rives LLP

(57) ABSTRACT

Medical appliances may be formed of multilayered constructs. The layers of the constructs may be configured with various physical properties or characteristics. The disposition and arrangement of each layer may be configured to create an overall construct with a combination of the individual properties of the layers. Constructs may be used to create vascular prostheses or other medical devices.

13 Claims, 5 Drawing Sheets

Related U.S. Application Data

(60) Provisional application No. 62/121,187, filed on Feb. 26, 2015.

(51) Int. Cl.
    *A61L 27/18*     (2006.01)
    *A61L 31/06*     (2006.01)
    *A61F 2/915*     (2013.01)

(52) U.S. Cl.
    CPC ............. *A61F 2250/0067* (2013.01); *A61F 2250/0069* (2013.01)

(56) References Cited

U.S. PATENT DOCUMENTS

| | | |
|---|---|---|
| 4,044,404 A | 8/1977 | Martin et al. |
| 4,096,227 A | 6/1978 | Gore |
| 4,127,706 A | 11/1978 | Martin et al. |
| 4,223,101 A | 9/1980 | Fine et al. |
| 4,323,525 A | 4/1982 | Bornat |
| 4,345,414 A | 8/1982 | Bornat et al. |
| 4,552,707 A | 11/1985 | How |
| 4,689,186 A | 8/1987 | Bornat |
| 4,758,223 A | 7/1988 | Rydell |
| 5,167,890 A | 12/1992 | Sasshofer et al. |
| 5,172,702 A | 12/1992 | Leigh |
| 5,236,447 A | 8/1993 | Kubo |
| 5,328,946 A | 7/1994 | Tuminello et al. |
| 5,344,297 A | 9/1994 | Hills |
| 5,509,902 A | 4/1996 | Raulerson |
| 5,512,051 A | 4/1996 | Wang et al. |
| 5,552,100 A | 9/1996 | Shannon et al. |
| 5,562,986 A | 10/1996 | Yamamoto et al. |
| 5,601,572 A | 2/1997 | Middleman et al. |
| 5,655,542 A | 8/1997 | Weilandt |
| 5,700,572 A | 12/1997 | Klatt et al. |
| 5,702,658 A | 12/1997 | Pellegrin et al. |
| 5,741,333 A | 4/1998 | Frid |
| 5,788,651 A | 8/1998 | Weilandt |
| 5,800,389 A | 9/1998 | Burney et al. |
| 5,810,870 A | 9/1998 | Myers et al. |
| 5,842,999 A | 12/1998 | Pruitt et al. |
| 5,941,910 A | 8/1999 | Schindler et al. |
| D418,223 S | 12/1999 | Phipps et al. |
| 6,010,529 A | 1/2000 | Herweck et al. |
| 6,045,567 A | 4/2000 | Taylor et al. |
| 6,053,943 A | 4/2000 | Edwin et al. |
| 6,075,180 A | 6/2000 | Sharber et al. |
| D428,150 S | 7/2000 | Ruf et al. |
| 6,106,913 A | 8/2000 | Scardino |
| 6,126,617 A | 10/2000 | Weilandt et al. |
| 6,165,212 A | 12/2000 | Dereume et al. |
| 6,196,978 B1 | 3/2001 | Weilandt et al. |
| 6,238,430 B1 | 5/2001 | Klumb |
| 6,273,861 B1 | 8/2001 | Bates et al. |
| 6,306,424 B1 | 10/2001 | Vyakarnam |
| 6,322,523 B2 | 11/2001 | Weilandt et al. |
| D457,955 S | 5/2002 | Bilitz |
| 6,383,214 B1 | 5/2002 | Banas et al. |
| 6,419,641 B1 | 7/2002 | Mark et al. |
| 6,436,135 B1 | 8/2002 | Goldfarb |
| D463,555 S | 9/2002 | Etter et al. |
| 6,488,662 B2 | 12/2002 | Sirimanne |
| 6,497,687 B1 | 12/2002 | Blanco |
| 6,498,207 B1 | 12/2002 | Hoshikawa et al. |
| 6,517,571 B1 | 2/2003 | Brauker et al. |
| 6,679,913 B2 | 1/2004 | Homsy |
| 6,719,783 B2 | 4/2004 | Lentz et al. |
| D490,152 S | 5/2004 | Myall et al. |
| 7,041,065 B2 | 5/2006 | Weilandt et al. |
| 7,115,220 B2 | 10/2006 | Dubson et al. |
| 7,118,698 B2 | 10/2006 | Armantrout et al. |
| 7,244,272 B2 | 7/2007 | Dubson et al. |
| 7,247,160 B2 | 7/2007 | Seiler et al. |
| 7,316,754 B2 | 1/2008 | Ide et al. |
| D571,009 S | 6/2008 | Smith et al. |
| 7,413,575 B2 | 8/2008 | Phaneuf et al. |
| 7,416,559 B2 | 8/2008 | Shalaby |
| D586,916 S | 2/2009 | Faulkner et al. |
| 7,485,141 B2 | 2/2009 | Majercak et al. |
| 7,498,079 B1 | 3/2009 | Donckers |
| 7,524,527 B2 | 4/2009 | Stenzel |
| 7,556,634 B2 | 7/2009 | Lee et al. |
| D598,543 S | 8/2009 | Vogel et al. |
| 7,582,240 B2 | 9/2009 | Marin et al. |
| 7,608,048 B2 | 10/2009 | Goldenberg |
| 7,655,175 B2 | 2/2010 | Michael et al. |
| D612,044 S | 3/2010 | Scheibe |
| D612,051 S | 3/2010 | Ruf |
| D619,251 S | 7/2010 | Justiniano-Garcia et al. |
| 7,799,261 B2 | 9/2010 | Orr et al. |
| D628,293 S | 11/2010 | Ruf |
| 7,857,608 B2 | 12/2010 | Fabbricante et al. |
| 7,914,568 B2 | 3/2011 | Cully et al. |
| 7,947,069 B2 | 5/2011 | Sanders |
| 7,981,353 B2 | 7/2011 | Mitchell et al. |
| 8,052,744 B2 | 11/2011 | Girton |
| 8,137,317 B2 | 3/2012 | Osypka |
| 8,178,030 B2 | 5/2012 | Anneaux et al. |
| 8,257,640 B2 | 9/2012 | Anneaux et al. |
| 8,262,979 B2 | 9/2012 | Anneaux et al. |
| 8,637,109 B2 | 1/2014 | Grewe et al. |
| 8,691,543 B2 | 4/2014 | Gaudette et al. |
| 8,771,582 B2 | 7/2014 | Phaneuf et al. |
| 9,034,031 B2 | 5/2015 | Anneaux |
| 9,198,999 B2 | 12/2015 | Hall |
| 9,392,998 B2 | 7/2016 | Snow |
| 9,655,710 B2 | 5/2017 | Eller |
| 9,775,933 B2 | 10/2017 | Knisley et al. |
| 9,856,588 B2 | 1/2018 | Anneaux |
| 10,010,395 B2 | 7/2018 | Puckett |
| 10,028,852 B2 * | 7/2018 | Hall ............... A61L 27/18 |
| 10,154,918 B2 | 12/2018 | Haselby et al. |
| 10,405,963 B2 | 9/2019 | Mcalpine |
| 10,675,850 B2 | 6/2020 | Hall et al. |
| 2001/0009979 A1 | 7/2001 | Weilandt et al. |
| 2001/0034549 A1 | 10/2001 | Bartholf et al. |
| 2001/0039446 A1 | 11/2001 | Edwin et al. |
| 2001/0049551 A1 | 12/2001 | Tseng et al. |
| 2001/0053929 A1 | 12/2001 | Vonesh et al. |
| 2002/0049489 A1 | 4/2002 | Herweck et al. |
| 2002/0077693 A1 | 6/2002 | Barclay |
| 2002/0082675 A1 | 6/2002 | Myers |
| 2002/0084178 A1 | 7/2002 | Dubson |
| 2002/0090725 A1 | 7/2002 | Simpson et al. |
| 2002/0107565 A1 | 8/2002 | Greenhalgh |
| 2002/0198588 A1 | 12/2002 | Armstrong et al. |
| 2003/0040772 A1 | 2/2003 | Hyodoh et al. |
| 2003/0050711 A1 | 3/2003 | Laurencin |
| 2003/0074049 A1 | 4/2003 | Hoganson |
| 2003/0100944 A1 | 5/2003 | Laksin et al. |
| 2003/0114917 A1 | 6/2003 | Holloway et al. |
| 2003/0139797 A1 | 7/2003 | Johnson |
| 2003/0195611 A1 | 10/2003 | Greenhalgh et al. |
| 2003/0211135 A1 | 11/2003 | Greenhalgh et al. |
| 2004/0030377 A1 | 2/2004 | Dubson et al. |
| 2004/0033364 A1 | 2/2004 | Spiridigliozzi et al. |
| 2004/0038038 A1 | 2/2004 | Yeung |
| 2004/0051201 A1 | 3/2004 | Greenhalgh et al. |
| 2004/0054397 A1 | 3/2004 | Smith et al. |
| 2004/0107004 A1 | 6/2004 | Levine et al. |
| 2004/0133124 A1 | 7/2004 | Bates et al. |
| 2004/0167606 A1 | 8/2004 | Chouinard |
| 2004/0215103 A1 | 10/2004 | Mueller et al. |
| 2004/0219345 A1 | 11/2004 | Armantrout et al. |
| 2005/0053782 A1 | 3/2005 | Sen et al. |
| 2005/0054947 A1 | 3/2005 | Goldenberg |
| 2005/0125017 A1 | 6/2005 | Kudrna et al. |
| 2005/0137675 A1 | 6/2005 | Dubson et al. |
| 2005/0187605 A1 | 8/2005 | Greenhalgh et al. |
| 2005/0244453 A1 | 11/2005 | Stucke et al. |
| 2005/0244639 A1 | 11/2005 | Marin et al. |
| 2005/0278018 A1 | 12/2005 | Jensen |
| 2006/0085019 A1 | 4/2006 | Cote et al. |

(56) References Cited

U.S. PATENT DOCUMENTS

| | | |
|---|---|---|
| 2006/0142852 A1 | 6/2006 | Sowinski et al. |
| 2006/0155210 A1 | 7/2006 | Beckman et al. |
| 2006/0200232 A1 | 9/2006 | Phaneuf et al. |
| 2006/0228435 A1 | 10/2006 | Andrady et al. |
| 2006/0233990 A1 | 10/2006 | Humphrey et al. |
| 2006/0259131 A1 | 11/2006 | Molaei et al. |
| 2006/0259137 A1 | 11/2006 | Artof et al. |
| 2006/0276874 A1 | 12/2006 | Wilson et al. |
| 2007/0026036 A1 | 2/2007 | Falotico et al. |
| 2007/0027407 A1 | 2/2007 | Miller |
| 2007/0031607 A1 | 2/2007 | Dubson et al. |
| 2007/0043428 A1 | 2/2007 | Jennings et al. |
| 2007/0078472 A1 | 4/2007 | Singh |
| 2007/0087027 A1 | 4/2007 | Greenhalgh et al. |
| 2007/0123973 A1 | 5/2007 | Roth |
| 2007/0142744 A1 | 6/2007 | Provencher |
| 2007/0142771 A1 | 6/2007 | Durcan |
| 2007/0179403 A1 | 8/2007 | Heske et al. |
| 2007/0198097 A1 | 8/2007 | Zegdi |
| 2007/0207179 A1 | 9/2007 | Andersen et al. |
| 2007/0207186 A1 | 9/2007 | Scanlon et al. |
| 2007/0244569 A1 | 10/2007 | Weber et al. |
| 2007/0250037 A1 | 10/2007 | Brimhall et al. |
| 2007/0269481 A1 | 11/2007 | Li et al. |
| 2007/0276477 A1 | 11/2007 | Lee et al. |
| 2008/0021545 A1 | 1/2008 | Reneker et al. |
| 2008/0029617 A1 | 2/2008 | Marshall et al. |
| 2008/0118541 A1 | 5/2008 | Pacetti |
| 2008/0119943 A1 | 5/2008 | Armstrong et al. |
| 2008/0199506 A1 | 8/2008 | Horres et al. |
| 2008/0200833 A1 | 8/2008 | Hardin et al. |
| 2008/0200835 A1 | 8/2008 | Monson et al. |
| 2008/0208323 A1 | 8/2008 | El-Kurdi et al. |
| 2008/0208325 A1 | 8/2008 | Helmus et al. |
| 2008/0228104 A1 | 9/2008 | Liber et al. |
| 2008/0234812 A1 | 9/2008 | Pacetti |
| 2008/0242171 A1 | 10/2008 | Huang et al. |
| 2008/0281223 A1 | 11/2008 | Goldenberg |
| 2008/0281406 A1 | 11/2008 | Addonizio et al. |
| 2008/0286321 A1 | 11/2008 | Reneker et al. |
| 2008/0288044 A1 | 11/2008 | Osborne |
| 2008/0300507 A1 | 12/2008 | Figueredo et al. |
| 2008/0305143 A1 | 12/2008 | Chen et al. |
| 2008/0319535 A1 | 12/2008 | Craven et al. |
| 2009/0012607 A1 | 1/2009 | Kim et al. |
| 2009/0018643 A1 | 1/2009 | Hashi et al. |
| 2009/0030499 A1 | 1/2009 | Bebb et al. |
| 2009/0082846 A1 | 3/2009 | Chobotov |
| 2009/0088828 A1 | 4/2009 | Shalev et al. |
| 2009/0127748 A1 | 5/2009 | Takahashi |
| 2009/0136651 A1 | 5/2009 | Larsen et al. |
| 2009/0143698 A1 | 6/2009 | Janssens |
| 2009/0160099 A1 | 6/2009 | Huang |
| 2009/0163994 A1 | 6/2009 | Quigley et al. |
| 2009/0227944 A1 | 9/2009 | Weber |
| 2009/0232920 A1 | 9/2009 | Lozano et al. |
| 2009/0248131 A1 | 10/2009 | Greenan |
| 2009/0248144 A1 | 10/2009 | Bahler et al. |
| 2009/0259200 A1 | 10/2009 | Lampropoulos et al. |
| 2009/0269429 A1 | 10/2009 | Lozano et al. |
| 2009/0280325 A1 | 11/2009 | Lozano et al. |
| 2009/0299220 A1 | 12/2009 | Field et al. |
| 2009/0319034 A1* | 12/2009 | Sowinski .......... B29C 43/003 623/1.46 |
| 2010/0013126 A1 | 1/2010 | Ishaque et al. |
| 2010/0042198 A1 | 2/2010 | Burton |
| 2010/0042199 A1 | 2/2010 | Burton |
| 2010/0063574 A1 | 3/2010 | Bogert |
| 2010/0076401 A1 | 3/2010 | Von Oepen et al. |
| 2010/0076543 A1 | 3/2010 | Melsheimer et al. |
| 2010/0093093 A1 | 4/2010 | Leong et al. |
| 2010/0129628 A1 | 5/2010 | Young |
| 2010/0130887 A1 | 5/2010 | Selis |
| 2010/0168773 A1 | 7/2010 | Funderburk et al. |
| 2010/0185156 A1 | 7/2010 | Kanner et al. |
| 2010/0190254 A1 | 7/2010 | Chian et al. |
| 2010/0193999 A1 | 8/2010 | Anneaux et al. |
| 2010/0233115 A1 | 9/2010 | Patel et al. |
| 2010/0280590 A1 | 11/2010 | Sun et al. |
| 2010/0304205 A1 | 12/2010 | Jo et al. |
| 2010/0323052 A1 | 12/2010 | Orr et al. |
| 2010/0331965 A1 | 12/2010 | Dugas et al. |
| 2011/0030885 A1 | 2/2011 | Anneaux et al. |
| 2011/0031656 A1 | 2/2011 | Anneaux et al. |
| 2011/0060276 A1 | 3/2011 | Schaeffer et al. |
| 2011/0087318 A1 | 4/2011 | Daugherty et al. |
| 2011/0089603 A1 | 4/2011 | Fabbricante et al. |
| 2011/0135806 A1 | 6/2011 | Grewe et al. |
| 2011/0142804 A1 | 6/2011 | Gaudette et al. |
| 2011/0152715 A1 | 6/2011 | Delap et al. |
| 2011/0156319 A1 | 6/2011 | Kurokawa et al. |
| 2011/0251631 A1 | 10/2011 | Trees et al. |
| 2011/0263456 A1 | 10/2011 | Harttig |
| 2011/0295200 A1 | 12/2011 | Speck et al. |
| 2011/0301696 A1 | 12/2011 | Mangiardi |
| 2012/0114722 A1 | 5/2012 | Ballard et al. |
| 2012/0201988 A1 | 8/2012 | Hansen et al. |
| 2012/0220894 A1 | 8/2012 | Melsheimer |
| 2012/0271396 A1 | 10/2012 | Zheng |
| 2012/0292810 A1 | 11/2012 | Peno et al. |
| 2012/0316633 A1 | 12/2012 | Flanagan et al. |
| 2013/0018220 A1 | 1/2013 | Vad |
| 2013/0023175 A1 | 1/2013 | Anneaux et al. |
| 2013/0053948 A1 | 2/2013 | Anneaux et al. |
| 2013/0059497 A1 | 3/2013 | Anneaux et al. |
| 2013/0079700 A1 | 3/2013 | Ballard et al. |
| 2013/0085565 A1 | 4/2013 | Eller et al. |
| 2013/0131548 A1 | 5/2013 | McGhie et al. |
| 2013/0150795 A1 | 6/2013 | Snow |
| 2013/0184808 A1 | 7/2013 | Hall et al. |
| 2013/0184810 A1 | 7/2013 | Hall et al. |
| 2013/0231733 A1 | 9/2013 | Knisley et al. |
| 2013/0238086 A1 | 9/2013 | Ballard et al. |
| 2013/0268062 A1 | 10/2013 | Puckett et al. |
| 2013/0316103 A1 | 11/2013 | Anneaux et al. |
| 2013/0324910 A1 | 12/2013 | Ohri et al. |
| 2014/0012304 A1 | 1/2014 | Lampropoulos et al. |
| 2014/0079758 A1 | 3/2014 | Hall et al. |
| 2014/0081414 A1 | 3/2014 | Hall et al. |
| 2014/0086971 A1 | 3/2014 | Hall et al. |
| 2014/0100479 A1 | 4/2014 | Tripp et al. |
| 2014/0171826 A1 | 6/2014 | Lampropoulos et al. |
| 2014/0207021 A1 | 7/2014 | Snow |
| 2014/0265061 A1 | 9/2014 | Hall et al. |
| 2014/0273703 A1 | 9/2014 | Mower et al. |
| 2015/0201963 A1 | 1/2015 | Snow |
| 2015/0045828 A1 | 2/2015 | McArthur et al. |
| 2015/0081000 A1 | 3/2015 | Hossainy |
| 2015/0094751 A1 | 4/2015 | Chen et al. |
| 2015/0134051 A1 | 5/2015 | Donadio et al. |
| 2015/0201917 A1 | 7/2015 | Snow |
| 2015/0320542 A1 | 11/2015 | Gabriele et al. |
| 2016/0250048 A1 | 9/2016 | Hall et al. |
| 2016/0331528 A1 | 11/2016 | Parker |
| 2017/0360993 A1 | 10/2017 | Argentine et al. |
| 2018/0064565 A1 | 3/2018 | Mactaggart |
| 2019/0060528 A1 | 2/2019 | Skender et al. |
| 2019/0076276 A1 | 3/2019 | Longo |
| 2019/0110911 A1 | 4/2019 | Nae |
| 2020/0015987 A1 | 1/2020 | Einav |
| 2020/0369016 A1 | 11/2020 | Hall et al. |
| 2020/0369017 A1 | 11/2020 | Hall et al. |
| 2020/0383767 A1 | 12/2020 | Eller et al. |

FOREIGN PATENT DOCUMENTS

| | | |
|---|---|---|
| CN | 1264571 | 9/2007 |
| CN | 101584612 | 11/2009 |
| EP | 0457456 | 11/1991 |
| EP | 0966920 B1 | 4/2004 |
| EP | 1605014 | 12/2005 |
| EP | 1679039 | 7/2006 |
| EP | 2363516 | 7/2011 |
| GB | 1577221 | 10/1980 |

(56) References Cited

FOREIGN PATENT DOCUMENTS

| | | |
|---|---|---|
| JP | 5140476 | 5/1975 |
| JP | 2007519491 | 7/2007 |
| JP | 2007531833 | 11/2007 |
| JP | 2009232882 | 10/2009 |
| JP | 2010517625 | 5/2010 |
| JP | 2010540190 | 12/2010 |
| JP | 2015504739 | 2/2015 |
| KR | 20100077913 | 7/2010 |
| KR | 20100108382 | 10/2010 |
| KR | 1020100108382 | 10/2010 |
| WO | 199622733 | 8/1996 |
| WO | 199800090 | 1/1998 |
| WO | 199944505 | 9/1999 |
| WO | 2003051233 | 6/2003 |
| WO | 2004090206 | 10/2004 |
| WO | 2005018600 | 3/2005 |
| WO | 2005074547 | 8/2005 |
| WO | 2005098100 | 10/2005 |
| WO | 2006013389 | 2/2006 |
| WO | 2006123340 | 11/2006 |
| WO | 2007075256 | 7/2007 |
| WO | 2008097592 | 8/2008 |
| WO | 2009046372 | 4/2009 |
| WO | 2009127170 | 10/2009 |
| WO | 2009146280 | 12/2009 |
| WO | 2010083530 | 7/2010 |
| WO | 2010132636 | 11/2010 |
| WO | 2011017698 | 2/2011 |
| WO | 2012103501 | 8/2012 |
| WO | 2012122485 | 9/2012 |
| WO | 2012167216 | 12/2012 |
| WO | 2013109528 | 7/2013 |
| WO | 2013151778 | 7/2013 |
| WO | 2014007979 | 1/2014 |

OTHER PUBLICATIONS

Office Action dated Jul. 11, 2019 for U.S. Appl. No. 14/081,715.
Office Action dated Aug. 7, 2019 for U.S. Appl. No. 15/806,020.
European Search Report dated Feb. 12, 2016 for EP13813055.4.
European Search Report dated Mar. 30, 2016 for EP13838784.0.
European Search Report dated Aug. 19, 2014 for EP12755426.9.
European Search Report dated Sep. 6, 2016 for EP14774594.7.
Extended European Search Report dated Mar. 30, 2016 for EP13838578.6.
Extended European Search Report dated Jun. 25, 2015 for EP12739348.6.
Extended European Search Report dated Jul. 26, 2016 for EP14741114.4.
International Preliminary Report dated Mar. 24, 2015 for PCT/US2013/060812.
International Preliminary Report dated Jul. 30, 2013 for PCT/US2012/023006.
International Preliminary Report on Patentability dated Mar. 24, 2015 for PCT/US2013/060062.
International Report on Patentability dated Jul. 22, 2014 for PCT/US2013/021554.
International Search Report and Written Opinion dated Apr. 3, 2014 for PCT/US2013/076418.
International Search Report and Written Opinion dated Apr. 26, 2013 for PCT/US2013/021554.
International Search Report and Written Opinion dated Apr. 27, 2015 for PCT/US2015/011746.
International Search Report and Written Opinion dated Apr. 30, 2015 for PCT/US2015/012002.
International Search Report and Written Opinion dated May 1, 2014 for PCT/US2014/012043.
International Search Report and Written Opinion dated May 23, 2012 for PCT/US2012/023006.
International Search Report and Written Opinion dated Jun. 8, 2016 for PCT/US2016/019487.
International Search Report and Written Opinion dated Jun. 23, 2015 for PCT/US2013/076418.
International Search Report and Written Opinion dated Jun. 26, 2014 for PCT/US2014/024868.
International Search Report and Written Opinion dated Jul. 1, 2014 for PCT/US2014/023416.
International Search Report and Written Opinion dated Jul. 1, 2016 for PCT/US2016/020165.
International Search Report and Written Opinion dated Sep. 6, 2013 for PCT/US2013/046245.
International Search Report and Written Opinion dated Dec. 3, 2013 for PCT/US2013/060172.
International Search Report and Written Opinion dated Dec. 5, 2013 for PCT/US2013/060812.
Notice of Allowance dated Jan. 25, 2017 for U.S. Appl. No. 14/152,626.
Notice of Allowance dated Apr. 3, 2018 for U.S. Appl. No. 14/081,504.
Notice of Allowance dated Apr. 14, 2015 for U.S. Appl. No. 14/031,746.
Notice of Allowance dated May 9, 2018 for U.S. Appl. No. 15/053,232.
Notice of Allowance dated Jul. 11, 2016 for U.S. Appl. No. 13/826,618.
Notice of Allowance dated Sep. 3, 2015 for U.S. Appl. No. 13/787,327.
Notice of Allowance dated Oct. 4, 2017 for U.S. Appl. No. 14/204,466.
Office Action dated Jan. 12, 2016 for U.S. Appl. No. 14/152,590.
Office Action dated Jan. 13, 2015 for U.S. Appl. No. 13/827,790.
Office Action dated Jan. 16, 2018 for U.S. Appl. No. 14/081,715.
Office Action dated Jan. 22, 2016 for U.S. Appl. No. 14/152,626.
Office Action dated Jan. 23, 2017 for U.S. Appl. No. 14/081,715.
Office Action dated Feb. 4, 2015 for U.S. Appl. No. 13/360,444.
Office Action dated Feb. 7, 2017 for U.S. Appl. No. 13/827,790.
Office Action dated Feb. 16, 2018 for U.S. Appl. No. 13/742,077.
Office Action dated Feb. 20, 2015 for U.S. Appl. No. 14/044,050.
Office Action dated Feb. 22, 2016 for U.S. Appl. No. 13/742,077.
Office Action dated Feb. 26, 2015 for U.S. Appl. No. 14/152,590.
Office Action dated Mar. 3, 2014 for U.S. Appl. No. 13/742,025.
Office Action dated Mar. 15, 2017 for U.S. Appl. No. 14/207,344.
Office Action dated Mar. 28, 2016 for U.S. Appl. No. 13/827,790.
Office Action dated Mar. 31, 2017 for U.S. Appl. No. 14/204,466.
Office Action dated Apr. 7, 2017 for U.S. Appl. No. 13/826,618.
Office Action dated Apr. 27, 2017 for U.S. Appl. No. 13/742,077.
Office Action dated May 9, 2014 for U.S. Appl. No. 13/360,444.
Notice of Allowance dated Mar. 13, 2020 for U.S. Appl. No. 14/832,422.
Office Action dated Mar. 25, 2020 for U.S. Appl. No. 14/081,715.
Office Action dated Apr. 6, 2020 for U.S. Appl. No. 13/827,790.
Board Decision on Appeal dated Nov. 23, 2018 for U.S. Appl. No. 14/044,050.
European Search Report dated Oct. 17, 2018 for EP16756335.2.
European Search Report dated Dec. 6, 2018 for EP13813055.4.
Office Action dated Jan. 2, 2009 for U.S. Appl. No. 13/360,444.
Office Action dated Jan. 2, 2019 for U.S. Appl. No. 14/152,590.
Office Action dated Jan. 10, 2019 for U.S. Appl. 13/826,618.
Office Action dated Jan. 17, 2019 for U.S. Appl. No. 14/832,422.
Office Action dated Feb. 8, 2019 for U.S. Appl. No. 14/081,715.
Notice of Allowance dated Oct. 9, 2019 for U.S. Appl. No. 13/826,618.
Office Action dated Oct. 7, 2019 for U.S. Appl. No. 13/360,444.
Office Action dated Oct. 7, 2019 for U.S. Appl. No. 14/152,590.
European Search Report dated Feb. 21, 2020 for EP19193202.9.
Notice of Allowance dated Jan. 30, 2020 for U.S. Appl. No. 14/152,590.
Notice of Allowance dated Feb. 6, 2020 for U.S. Appl. No. 13/360,444.
Office Action dated Feb. 20, 2020 for U.S. Appl. No. 15/806,020.
Office Action dated May 11, 2018 for U.S. Appl. No. 13/826,618.
Office Action dated May 11, 2018 for U.S. Appl. No. 14/832,422.
Office Action dated May 19, 2017 for U.S. Appl. No. 13/742,025.
Office Action dated Jun. 1, 2016 for U.S. Appl. No. 14/134,280.
Office Action dated Jun. 8, 2016 for U.S. Appl. No. 14/044,050.
Office Action dated Jun. 9, 2016 for U.S. Appl. No. 14/152,626.
Office Action dated Jun. 15, 2018 for U.S. Appl. No. 14/207,344.

(56) References Cited

OTHER PUBLICATIONS

Office Action dated Jun. 19, 2017 for U.S. Appl. No. 14/081,504.
Office Action dated Jun. 23, 2017 for U.S. Appl. No. 13/829,493.
Office Action dated Jun. 28, 2018 for U.S. Appl. No. 14/081,715.
Office Action dated Jun. 29, 2017 for U.S. Appl. No. 14/081,715.
Office Action dated Jun. 30, 2016 for U.S. Appl. No. 14/081,715.
Office Action dated Jul. 2, 2014 for U.S. Appl. No. 14/044,050.
Office Action dated Jul. 12, 2017 for U.S. Appl. No. 15/053,232.
Office Action dated Jul. 13, 2018 for U.S. Appl. No. 13/827,790.
Office Action dated Jul. 26, 2017 for U.S. Appl. No. 13/827,790.
Office Action dated Jul. 26, 2018 for U.S. Appl. No. 14/152,590.
Office Action dated Jul. 29, 2015 for U.S. Appl. No. 14/152,626.
Office Action dated Aug. 6, 2018 for U.S. Appl. No. 13/360,444.
Office Action dated Aug. 10, 2015 for U.S. Appl. No. 14/044,050.
Office Action dated Aug. 29, 2014 for U.S. Appl. No. 14/152,590.
Office Action dated Sep. 9, 2016 for U.S. Appl. No. 14/081,504.
Office Action dated Sep. 9, 2016 for U.S. Appl. No. 14/207,344.
Office Action dated Sep. 11, 2017 for U.S. Appl. No. 14/832,422.
Office Action dated Sep. 23, 2016 for U.S. Appl. No. 14/152,590.
Office Action dated Sep. 24, 2014 for U.S. Appl. No. 14/031,746.
Office Action dated Sep. 27, 2016 for U.S. Appl. No. 13/827,790.
Office Action dated Sep. 28, 2017 for U.S. Appl. No. 14/207,344.
Office Action dated Oct. 6, 2016 for U.S. Appl. No. 13/360,444.
Office Action dated Oct. 6, 2016 for U.S. Appl. No. 13/742,025.
Office Action dated Oct. 10, 2014 for U.S. Appl. No. 13/742,025.
Office Action dated Oct. 15, 2015 for U.S. Appl. No. 13/827,790.
Office Action dated Oct. 20, 2017 for U.S. Appl. No. 13/826,618.
Office Action dated Oct. 26, 2016 for U.S. Appl. No. 13/742,077.
Office Action dated Nov. 2, 2015 for U.S. Appl. No. 13/742,077.
Office Action dated Nov. 17, 2016 for U.S. Appl. No. 13/829,493.
Office Action dated Nov. 17, 2017 for U.S. Appl. No. 13/360,444.
Office Action dated Nov. 18, 2016 for U.S. Appl. No. 13/826,618.
Office Action dated Nov. 20, 2015 for U.S. Appl. No. 13/826,618.
Office Action dated Nov. 21, 2017 for U.S. Appl. No. 14/152,590.
Office Action dated Dec. 18, 2015 for U.S. Appl. No. 14/081,504.
Office Action dated Dec. 28, 2017 for U.S. Appl. No. 13/827,790.
Office Action dated Dec. 29, 2017 for U.S. Appl. No. 14/081,504.
Shuttle® and CT-Core® Semi-Automatic Devices Updated to the website between Nov. 8, 2012-Jan. 24, 2013. Accessed website on Jun. 27, 2014 at http://www.healthcare.com/qb/int_radiplogy.html.
Office Action dated Jan. 14, 2019 for U.S. Appl. No. 13/827,790.
Notice of Allowance dated Dec. 14, 2020 for U.S. Appl. No. 14/081,715.
Notice of Allowance dated Dec. 15, 2020 for U.S. Appl. No. 15/806,020.
European Search Report dated Jun. 16, 2014 for EP14160501.4.
International Search Report and Written Opinion dated Sep. 17, 2013 for PCT/US2013/060172.
Office Action dated Jul. 30, 2020 for U.S. Appl. No. 15/806,020.
European Search Report dated Feb. 03, 2021 for EP20191283.9.
European Search Report dated Dec. 23, 2020 for EP20199088.4.
Office Action dated Dec. 23, 2020 for U.S. Appl. No. 13/827,790.
Yasuda, et al., Contact Angle of Water on Polymer Surfaces, Am Chem, Langmuir, vol. 10 No. 7, 1994.
European Search Report dated Jan. 28, 2021 for EP20190128.7.

\* cited by examiner

LAYERED MEDICAL APPLIANCES AND METHODS

RELATED APPLICATIONS

The present application is a continuation of U.S. application Ser. No. 15/053,232, filed on Feb. 25, 2016, titled, "Layered Medical Appliances and Methods," which claims the benefit of U.S. Provisional Application No. 62/121,187, filed on Feb. 26, 2015, titled, "Layered Medical Appliances and Methods," the disclosure of each of which is incorporated herein by reference in its entirety.

TECHNICAL FIELD

The present disclosure relates generally to medical appliances, including medical appliances composed of two or more layers of material. Medical appliances within the scope of this disclosure may include porous layers, nonporous layers, fluid or cellular impermeable layers, and so forth. These layers may be included and/or arranged within the construct to affect the structural properties and/or biocompatibility of the medical appliance.

BRIEF DESCRIPTION OF THE DRAWINGS

The embodiments disclosed herein will become more fully apparent from the following description and appended claims, taken in conjunction with the accompanying drawings. These drawings depict only typical embodiments, which will be described with additional specificity and detail through use of the accompanying figures in which:

DETAILED DESCRIPTION

Figure 1:
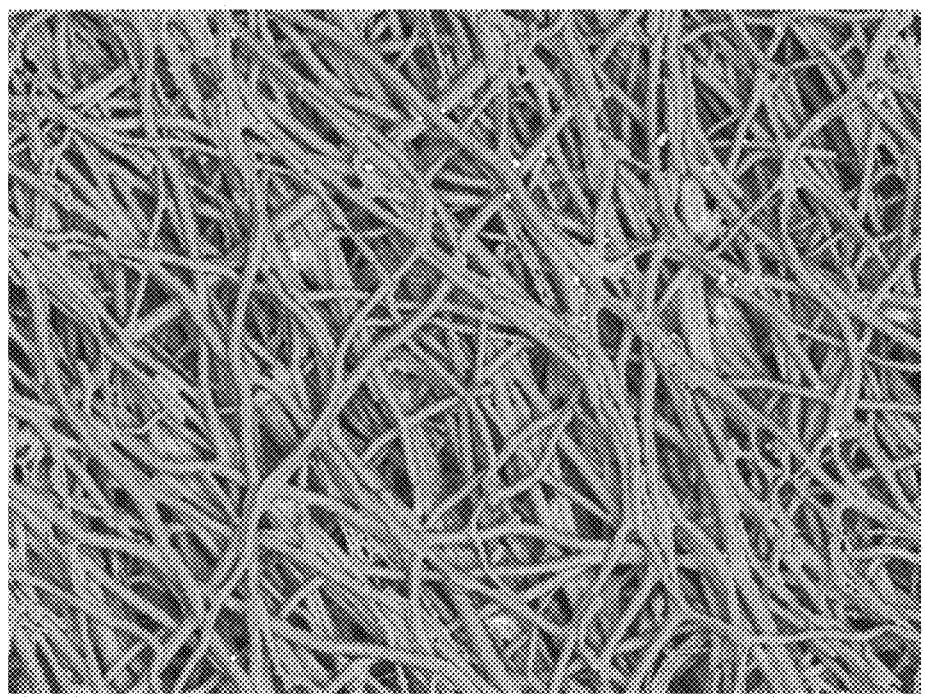
FIG. 1 is a Scanning Electron Micrograph (SEM) (950×) of a serially deposited polytetrafluoroethylene (PTFE) fiber mat.

Medical appliances may be deployed in various body lumens for a variety of purposes. Stents and/or stent-grafts may be deployed, for example, in the vascular system for a variety of therapeutic purposes, including the treatment of occlusions within the lumens of that system. The current disclosure may be applicable to stents, stent-grafts, or other medical appliances designed for the central venous ("CV") system, peripheral vascular ("PV") stents, abdominal aortic aneurysm ("AAA") stents, bronchial stents, esophageal stents, biliary stents, coronary stents, gastrointestinal stents, neuro stents, thoracic aortic endographs, or any other stent or stent-graft. Further, the present disclosure may be equally applicable to other prostheses such as grafts, shunts, and so forth. Additionally, medical appliances comprising a continuous lumen wherein a portion of the longitudinal length is reinforced, for example by a metal scaffold, and a portion of the longitudinal length has no scaffold are also within the scope of this disclosure. Any medical appliance composed of materials herein described may be configured for use or implantation within various areas of the body, including vascular, cranial, thoracic, pulmonary, esophageal, abdominal, or ocular application. Examples of medical appliances within the scope of this disclosure include, but are not limited to, stents, vascular grafts, stent-grafts, cardiovascular patches, reconstructive tissue patches, hernia patches, general surgical patches, heart valves, sutures, dental reconstructive tissues, medical device coverings and coatings, gastrointestinal devices, blood filters, artificial organs, ocular implants, and pulmonary devices, including pulmonary stents. For convenience, many of the specific examples included below reference stent-grafts. Notwithstanding any of the particular medical appliances referenced in the examples or disclosure below, the disclosure and examples may apply analogously to any prostheses or other medical appliance.

As used herein, the terms stent and stent-graft refer to medical appliances configured for use within bodily structures, such as within body lumens. A stent or stent-graft may comprise a scaffolding or support structure, such as a frame, and/or a covering.

It will be readily understood that the components of the embodiments as generally described and illustrated in the Figures herein could be arranged and designed in a wide variety of different configurations. Thus, the following more detailed description of various embodiments, as represented in the Figures, is not intended to limit the scope of the disclosure, but is merely representative of various embodiments. While the various aspects of the embodiments are presented in drawings, the drawings are not necessarily drawn to scale unless specifically indicated.

The phrases" "coupled to" and "in communication with" refer to any form of interaction between two or more entities, including mechanical, electrical, magnetic, electromagnetic, fluid, and thermal interaction. Two components may be coupled to each other even though they are not in direct contact with each other. For example, two components may be coupled to each other through an intermediate component.

The directional terms "proximal" and "distal" are used herein to refer to opposite locations on a stent or another medical appliance. The proximal end of an appliance is defined as the end closest to the practitioner when the appliance is disposed within a deployment device which is being used by the practitioner. The distal end is the end opposite the proximal end, along the longitudinal direction of the appliance, or the end furthest from the practitioner. It is understood that, as used in the art, these terms may have different meanings once the appliance is deployed (i.e., the "proximal" end may refer to the end closest to the head or heart of the patient depending on application). For consistency, as used herein, the ends labeled "proximal" and "distal" remain the same regardless of whether the appliance is deployed.

The longitudinal direction of a stent or stent-graft is the direction along the axis of a generally tubular stent or stent-graft. In embodiments where an appliance is composed of a metal wire structure coupled to one or more layers of a film or sheet-like component, such as a polymer layer, the metal structure is referred to as the "scaffolding" or "frame," and the polymer layer as the "covering" or "coating." The terms "covering" and "coating" may refer to a single layer of polymer, multiple layers of the same polymer, or layers comprising distinct polymers used in combination. Furthermore, as used herein, the terms "covering" and "coating"

refer only to a layer or layers which are coupled to a portion of the scaffold; neither term requires that the entire scaffold be "covered" or "coated." In other words, medical appliances wherein a portion of the scaffold may be covered and a portion may remain bare are within the scope of this disclosure. Finally, any disclosure recited in connection with coverings or coatings may analogously be applied to medical devices comprising one or more "covering" layers with no associated frame or other structure. For example, a hernia patch comprising any of the materials described herein as "coatings" or "coverings" is within the scope of this disclosure regardless of whether the patch further comprises a frame or other structure. Similarly, a tubular graft or shunt may be comprised of the covering or layered materials recited herein, with no associated scaffolding structure.

Medical device coverings may comprise multilayered constructs, comprised of two or more layers which may be serially applied. Further, multilayered constructs may comprise nonhomogeneous layers, meaning adjacent layers have differing properties. Thus, as used herein, each layer of a multilayered construct may comprise a distinct layer, either due to the distinct application of the layers or due to differing properties between layers. As layers may be identified by their position, structure, or function, an individual layer may not necessarily comprise only a single material or a single microstructure.

Additionally, as used herein, "tissue ingrowth" and "cellular penetration" refer to any presence or penetration of a biological or bodily material into a component of a medical appliance. For example, the presence of body tissues (e.g., collagen, cells, and so on) within an opening or pore of a layer or component of a medical appliance comprises tissue ingrowth into that component. Further, as used herein, "attachment" of tissue to a component of a medical appliance refers to any bonding or adherence of a tissue to the appliance, including indirect bonds. For example, tissue of some kind (e.g., collagen) may become attached to a stent covering (including attachment via tissue ingrowth), and another layer of biologic material (such as endothelial cells) may, in turn, adhere to the first tissue. In such instances, the second biologic material (endothelial cells in the example) and the tissue (collagen in the example) are "attached" to the stent covering.

Porous materials may be selectively permeable to various particles or biologic elements based on the pore sizes of the material. For example, materials with pore sizes smaller than 20 micron may be impermeable to cells types larger than 20 micron, such as foreign body giant cells. Similarly, materials with pore sizes smaller than eight micron may be impermeable to penetration by other cell types, such as red blood cells. In some embodiments, materials with pore sizes smaller than eight micron or smaller than six micron (including, for example, any value between zero and eight micron) may be impermeable to red blood cells.

As used herein, cellular impermeability does not require the complete exclusion of any cellular migration across a barrier. A material may be impermeable to red blood cell migration, for example, even if a small number of red bloods cells are able to cross the material. Accordingly, materials may be configured to substantially inhibit cellular migration across the material while meeting the definition of cellular impermeability.

As used herein, red blood cell impermeable materials are materials which substantially inhibit the transmural migration of red blood cells. Moreover, as used herein, to substantially inhibit transmural migration of red blood cells means that, under biologic pressure (such as when implanted in the body), less than 0.1% of red blood cells which contact the material wall will migrate across the material wall. Accordingly, this definition includes materials that inhibit the transmural migration of the majority of red blood cells, without requiring complete restriction of all such cells. In some instances, materials with pore sizes smaller than eight micron, including pore sizes smaller than six micron, or pore sizes of any value between zero and eight micron may be impermeable to transmural migration of red blood cells. Other materials, for example, composite materials having individual layers of differing pore sizes, may likewise be impermeable to transmural migration of red blood cells.

In some instances, layers with porosities greater than six or eight micron, when combined with additional layers to create a more tortuous transmural path, may be impermeable to transmural migration of red blood cells across the combined layers, even if no single layer has a porosity less than eight micron.

Still further, composite constructs comprising various layers of various porosities may be impermeable to transmural migration of red blood cells. In some embodiments, a construct comprised of layers of varying porosities, coupled to a substantially nonporous layer may be impermeable to transmural migration of red blood cells.

Moreover, constructs within the scope of this disclosure may be cell impermeable to any cell type, meaning that less than 0.1% of cells which contact the construct (regardless of the cell type), will migrate across the construct wall. Similarly, constructs within the scope of this disclosure may be tissue impermeable, meaning that less than 0.1% of the mass or volume of tissue which contacts the construct will migrate across the construct wall.

In one example, a cell impermeable tubular multilayered construct was implanted in an animal host for 30 days. Upon removal of the multilayered construct, no measurable amount of tissue was present on the lumenal surface of the construct. Accordingly, materials implanted in an animal host for 30 days with no measurable transmural cell or tissue migration are cellular and tissue impermeable, as those terms are used herein. It was also observed that standard ePTFE stent-graft exhibited tissue growth on the lumenal surface when similarly implanted.

Additionally, materials or constructs may be impermeable to fluidic passage across the material wall. Materials or layers with pore sizes smaller than 0.5 micron are herein referenced as being impermeable to fluidic passage, or fluid impermeable across the material or layer.

The pore sizes associated with any of the embodiments above may refer to average pore size as further defined below. It may also refer to pore sizes determined by direct measurement techniques. The terms "generally" and "substantially" as used herein indicate that a parameter is within 5% of a reference parameter. Thus, two quantities termed as generally equivalent are within 5% of each other. Further, a generally or substantially impermeable membrane only varies from the defined pore sizes above by 5%.

Lumens within the circulatory system are generally lined with a single layer (monolayer) of endothelial cells. This lining of endothelial cells makes up the endothelium. The endothelium acts as an interface between blood flowing through the lumens of the circulatory system and the inner walls of the lumens. The endothelium, among other functions, reduces or prevents turbulent blood flow within the lumen. The endothelium plays a role in many aspects of vascular biology, including atherosclerosis, creating a selective barrier around the lumen, blood clotting, inflammation, angiogenesis, vasoconstriction, and vasodilation.

A therapeutic medical appliance which includes a covering of porous or semi-porous material may permit the formation of an endothelial layer onto the porous surface of the blood contact side of the medical device. Formation of an endothelial layer on a surface, or endothelialization, may increase the biocompatibility of an implanted device. For example, a stent which permits the formation of the endothelium on the inside diameter (blood contacting surface) of the stent may further promote healing at the therapeutic region and/or have longer-term viability. For example, a stent coated with endothelial cells may be more consistent with the surrounding body lumens, thereby resulting in less turbulent blood flow or a decreased risk of thrombosis, or the formation of blood clots. A stent or stent-graft which permits the formation of an endothelial layer on the inside surface of the stent may therefore be particularly biocompatible, resulting in less trauma at the point of application, fewer side effects, and/or longer-term device viability. Medical appliances including a covering of porous or semi-porous material may be configured to inhibit or reduce inflammatory responses by the body toward the tissue-contacting side of the medical appliance, for example. Mechanisms such as an inflammatory response by the body toward the medical appliance may stimulate, aggravate, or encourage negative outcomes, such as neointimal hyperplasia. For example, a device configured to permit tissue ingrowth and/or the growth or attachment of endothelial cells onto the blood-contacting side of the device may reduce the likelihood of negative flow characteristics and blood clotting. Similarly, a device so configured may mitigate the body's inflammatory response toward the material on, for example, the tissue-contacting side of the device. By modulating the evoked inflammatory response, negative outcomes such as the presence of bioactive inflammatory macrophages and foreign body giant cells may be reduced. This may aid in minimizing the chemical chain of responses that may encourage fibrous capsule formation surrounding the device and events stimulating neointimal hyperplasia.

Serially deposited fibers, such as rotational spun or electrospun materials, such as those described herein, may be used to comprise portions of medical appliances, such as stents, patches, grafts, and so forth. The present disclosure is applicable to any implantable medical appliance, notwithstanding any specific examples included below. In other words, though particular medical appliances, such as stents or patches, may be referenced in the disclosure and examples below, the disclosure is also analogously applicable to other medical appliances, such as those which comprise a covering or layer of polymeric material.

In some embodiments, serially deposited nanofibers (and/ or microfibers) may be configured to permit interaction with nano-scale (and/or micro-scale) body structures, such as endothelial cells, red blood cells, collagen, and so forth.

Medical appliances may comprise two or more layers or materials. These layers, alone or in combination, may be designed or configured to impart various properties to the overall construct. For example, one or more layers, and/or the combined characteristics of two or more layers, may control the structural properties of the overall construct, such as tensile strength, burst strength, flexibility, hoop strength, resistance to radial compression, and so forth. Similarly, one or more layers, and/or the combined characteristics of two or more layers, may control the biocompatibility of the medical appliance. For example, porosity, fluid permeability, cellular permeability, and so forth may all affect the biologic response to a medical appliance deployed within a patient's body.

Various structures, including medical appliances and related components, may comprise serially deposited fibers. Serially deposited fibers may comprise polymeric fibers, ceramic fibers, and/or other materials. In some embodiments, soft or fluidic materials are deposited in elongate strands or fibers on a collector or substrate. After these fibers are deposited, the shape or structure of the mat or lattice of fibers may be set by, for example, hardening of the material of the fibers. For example, polymeric materials may be deposited as fibers in the form of a polymeric dispersion and then heated to remove the solvent component of the dispersion and to set the structure of the polymeric fibers. Similarly, polymeric materials may be serially deposited as fibers while the material is in a heated or molten state. Cooling of the collected fibers may tend to set the structure of the mat or lattice of fibers. The fibers comprising these mats or lattices may generally be on a micro scale (fibers which are between one micron and one millimeter in diameter) and/or generally on a nano scale (fibers which are smaller than one micron in diameter). FIG. 1 is an SEM (950×) of an exemplary serially deposited fiber mat. The fibers of the mat of FIG. 1 were deposited by rotational spinning of polytetrafluoroethylene (PTFE).

Serially deposited fiber mats or lattices refer to structures composed at least partially of fibers successively deposited on a collector, on a substrate, on a base material, and/or on previously deposited fibers. In some instances, the fibers may be randomly disposed, while in other embodiments the alignment or orientation of the fibers may be somewhat controlled or follow a general trend or pattern. Regardless of any pattern or degree of fiber alignment, because the fibers are deposited on the collector, substrate, base material, and/or previously deposited fibers, the fibers are not woven, but rather serially deposited. Because such fibers are configured to create a variety of structures, as used herein, the terms "mat" and "lattice" are intended to be broadly construed as referring to any such structure, including tubes, spheres, sheets, and so on. Furthermore, the term "membrane" as used herein refers to any structure comprising serially deposited fibers having a thickness which is smaller than at least one other dimension of the membrane. Examples of membranes include, but are not limited to, serially deposited fiber mats or lattices forming sheets, strips, tubes, spheres, covers, layers, and so forth.

Rotational spinning is one example of how a material may be serially deposited as fibers. One embodiment of a rotational spinning process comprises loading a polymer solution or dispersion into a cup or spinneret configured with orifices on the outside circumference of the spinneret. The spinneret is then rotated, causing (through a combination of centrifugal and hydrostatic forces, for example) the flowable material within the spinneret to be expelled from the orifices. The material may then form a "jet" or "stream" extending from the orifice, with drag forces tending to cause the stream of material to elongate into a small diameter fiber. The fibers may then be deposited on a collection apparatus, a substrate, or other fibers. Once collected, the fibers may be dried, cooled, sintered, or otherwise processed to set the structure or otherwise harden the fiber mat. For example, polymeric fibers rotational spun from a dispersion may be sintered to remove solvents, fiberizing agents, or other materials as well as to set the structure of the mat. In one embodiment, for instance, an aqueous polytetrafluoroethylene (PTFE) dispersion may be mixed with polyethylene oxide (PEO) (as a fiberizing agent) and water (as a solvent for the PEO), and the mixture rotational spun. Sintering by heating the collected fibers may set the PTFE structure, evaporate off the water, and sublimate the PEO. Exemplary methods and systems for rotational spinning can be found in U.S. patent application Ser. No. 13/742,025, filed on Jan. 15, 2013, and titled "Rotational Spun Material Covered Medical Appliances and Methods of Manufacture," which is herein incorporated by reference in its entirety.

Rotational spinning processes and electrospinning processes may produce serially deposited fiber mats with differing characteristics. For example, as compared to electrospinning processes, rotational spinning may exhibit superior yield, performance, and scaling. Rotational spinning processes may exhibit greater repeatability, reliability, and quality compared to electrospinning. In other words, rotational spun fiber mats may exhibit more consistency within closer tolerances as compared to electrospun fiber mats. Rotational spinning may be more directly scalable to large operations. Whereas electrospinning on a large scale may entail high voltage and other difficulties that further introduce time, cost, and variability, rotational spinning may more directly and simply scale, producing more consistent fiber mats.

Electrospinning is another embodiment of how a material may be serially deposited as fibers. One embodiment of an electrospinning process comprises loading a polymer solution or dispersion into a syringe coupled to a syringe pump. The material is forced out of the syringe by the pump in the presence of an electric field. The material forced from the syringe may elongate into fibers that are then deposited on a grounded collection apparatus, such as a collector or substrate. The system may be configured such that the material forced from the syringe is electrostatically charged, and thus attracted to the grounded collection apparatus. As with rotational spinning, once collected, the fibers may be dried, cooled, sintered, or otherwise processed to set the structure or otherwise harden the fiber mat. For example, polymeric fibers electrospun from a dispersion may be sintered to remove solvents, fiberizing agents, or other materials as well as to set the structure of the mat. As in rotational spinning, one embodiment of electrospinning comprises electrospinning an aqueous PTFE dispersion mixed with PEO and water (as a solvent for the PEO). Sintering by heating the collected fibers may set the PTFE structure, evaporate off the water, and sublimate the PEO. Exemplary methods and systems for electrospinning medical devices can be found in U.S. patent application Ser. Nos. 13/826,618 and 13/827,790, both filed on Mar. 13, 2014, and both titled "Electrospun Material Covered Medical Appliances and Methods of Manufacture," and U.S. patent application Ser. No. 13/360,444, filed on Jan. 27, 2012, and titled "Electrospun PTFE Coated Stent and Method of Use," each of which is hereby incorporated by reference in its entireties.

Rotational spinning and/or electrospinning may be utilized to create a variety of materials or structures comprising serially deposited fibers. The microstructure or nanostructure of such materials, as well as the porosity, permeability, material composition, rigidity, fiber alignment, and so forth, may be controlled or configured to promote biocompatibility or influence interactions between the material and cells or other biologic material. A variety of materials may be serially deposited through processes such as rotational spinning and electrospinning: for example, polymers, ceramics, metals, materials which may be melt-processed, or any other material having a soft or liquid form. A variety of materials may be serially deposited through rotational spinning or electrospinning while the material is in a solution, dispersion, molten or semi-molten form, and so forth. The present disclosure may be applicable to any material discussed herein being serially deposited as fibers onto any substrate or in any geometry discussed herein. Thus, examples of particular materials or structures given herein may be analogously applied to other materials and/or structures.

Rotational spinning, electrospinning, or other analogous processes may be used to create serially deposited fiber mats as disclosed herein. Throughout this disclosure, examples may be given of serially deposited fiber mats generally, or the examples may specify the process (such as rotational spinning or electrospinning) utilized to create the serially deposited fiber mat. It is within the scope of this disclosure to analogously apply any process for creating serially deposited fibers to any disclosure or example below, regardless of whether the disclosure specifically indicates a particular mat was formed according to a particular process.

Figure 2:
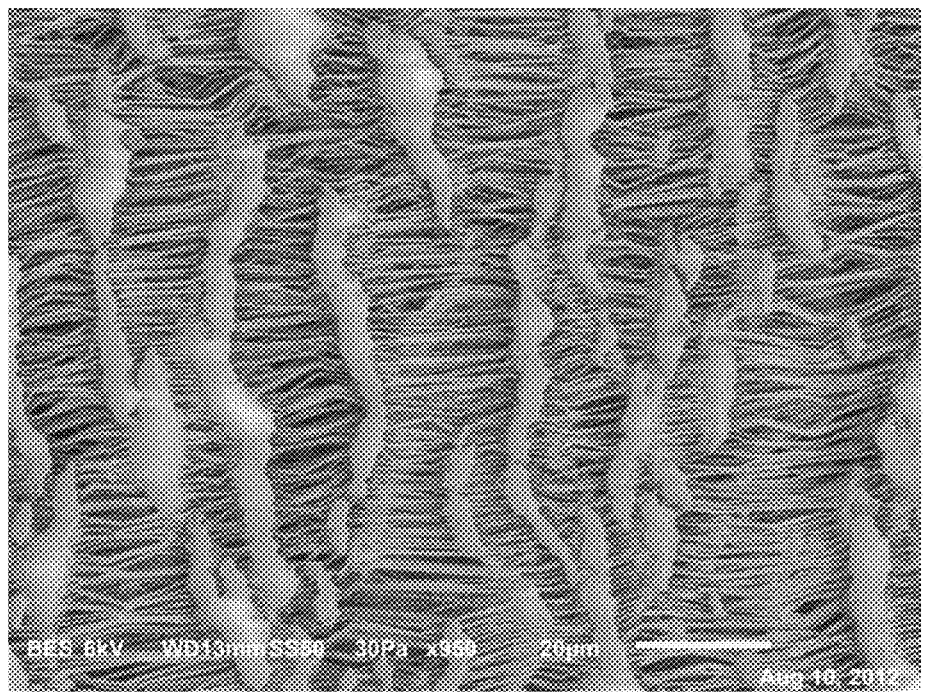
FIG. 2 is a Scanning Electron Micrograph (SEM) (950×) of an expanded polytetrafluoroethylene (ePTFE) mat.

Expanded polytetrafluoroethylene (ePTFE) may also be used as a component of a layered medical appliance in some embodiments. ePTFE may be formed when a sheet of PTFE is heated and stretched. The sheet of ePTFE may be formed, for example, by extrusion or other methods. Heating and stretching of the PTFE sheet to form ePTFE changes the microstructure of the sheet, making it more porous and creating nodes of material with fibrils of material extending there between. U.S. Pat. No. 3,664,915 of W. L. Gore describes various processes for heating and stretching PTFE to create ePTFE. In some processes, the ePTFE will be expanded to a greater extent along a longitudinal direction as compared to a transverse direction. Thus some ePTFE mats may be described as having an axis of expansion, or the direction in which the majority of the expansion was done. In some instances the ratio of expansion in the longitudinal direction to expansion in a transverse direction may be between 10:1 and 20:1. FIG. 2 is an exemplary SEM (950×) of an ePTFE membrane.

In some applications, ePTFE may also be further processed after it has been initially formed. Some such processes may densify the ePTFE, reducing the porosity and increasing the strength. In some instances such post-processing may be used to contract fibrils extending between the nodes of the ePTFE to create a layer that is substantially impermeable to tissue and/or fluid. Thus, ePTFE layers may be configured with various permeability characteristics, including layers which are impermeable to cellular or tissue migration across the layer. Further, such post-processing may increase the strength of the layer due to the resulting work processing stresses created in the material.

Characteristics of mats, including serially deposited fibers and/or ePTFE, may be determined in a variety of ways. For example, internodal distance, or IND, of ePTFE can be used to characterize the degree of expansion and/or the porosity of the ePTFE. The internodal distance refers to the average distance between adjacent nodes of the membrane.

Percent porosity is another measurement that may be used to characterize membranes with porous sections. This method can be used, for example, to characterize ePTFE and/or serially deposited fibers. Percent porosity refers to the percent of open space to closed space (or space filled by fibers) in a membrane or mat. Thus, the more open the structure is, the higher the percent porosity measurement. In some instances, percent porosity may be determined by first obtaining an image, such as an SEM, of a material. The image may then be converted to a "binary image," or an image showing only black and white portions, for example. The binary image may then be analyzed and the percent porosity determined by comparing the relative numbers of each type of binary pixel. For example, an image may be converted to a black and white image wherein black portions represent gaps or holes in the membrane while white portions represent the fibers or other structure of the membrane. Percent porosity may then be determined by dividing the number of black pixels by the number of total pixels in the image. In some instances, a code or script may be configured to make these analyses and calculations.

In some embodiments the "average pore size" of an ePTFE of serially deposited mat may be used as an alternate or additional measurement of the properties of the mat. The complex and random microstructure of serially deposited mats, for example, presents a challenge to the direct measurement of the average pore size of the mat. Average pore size can be indirectly determined by measuring the permeability of the mat to fluids using known testing techniques and instruments. Once the permeability is determined, that measurement may be used to determine an "effective" pore size of the serially deposited mat. As used herein, the "pore size" of a serially deposited mat and/or an expanded membrane refers to the pore size of a known membrane which corresponds to the permeability of the serially deposited or expanded fabric when measured using ASTM standard F316 for the permeability measurement. This standard is described in ASTM publication F316 "Standard Test Methods for Pore Size Characteristics of Membrane Filters by Bubble Point and Mean Flow Pore Test," which is incorporated herein by reference. In some instances this test can be used as a quality control after configuring a mat based on other measurements such as percent porosity.

Further, average pore diameter and average pore area of an ePTFE or serially deposited mat may be calculated programmatically using software to analyze an image, such as an SEM. For example, an SEM may be evaluated using software analysis to measure various characteristics of a material layer. As part of this exemplary process, the SEM image may first be converted to a "binary image," or an image showing only black and white portions, as discussed above. The binary image may then be analyzed, the fibers or other features of the layer identified, and characteristics determined by comparing the relative numbers and placements of each type of binary pixel. For example, an image may be converted to a black and white image wherein black portions represent gaps or holes in a serially deposited fiber mat while white portions represent the fibers of the mat. The software thus identifies the presence and position of fibers and pores or open portions of the fiber mat.

Characteristics such as fiber width and pore size may be determined by analyzing these binary images. Still further, characteristics of relative fibers, such as the number of fiber branches, intersections, bundles, fiber density, and so forth, may be determined through similar analysis. In some instances, a code or script may be configured to make various analyses and calculations. U.S. patent application Ser. No. 14/207,344, titled "Serially Deposited Fiber Materials and Associated Devices and Methods," filed on Mar. 12, 2014, which is hereby incorporated by reference in its entirety, discusses various methods of characterizing and evaluating construct layers.

In determining average pore size, an image may be evaluated to distinguish between areas comprising fibers and open areas, such as by creating a binary image as discussed above. Pores, or areas within a fiber mat encapsulated by intersecting or branched fibers, may then be identified. To determine the average pore diameter, a large sample of pores may be randomly selected from the target image. In some instances, between 50 and 300 pores may comprise the sample. The diameter of a particular pore may be calculated by tracing multiple diameters of equal angular spacing around the pore through the centroid of the pore. In some embodiments, 30 such diameters were used to determine a calculated pore size. The measured diameters are then averaged to determine the calculated effective diameter of the pore. The area of each identified pore may also be computed based on the pixel area of each pore. Each pore identified for sampling may be manually checked to confirm proper identification of pores. The average pore diameter of a fiber mat may then be computed by averaging the calculated effective diameters of the identified pore. Again, material total porosity may also be determined by the percentage of dark pixels to light pixels in the image.

Figure 3A:
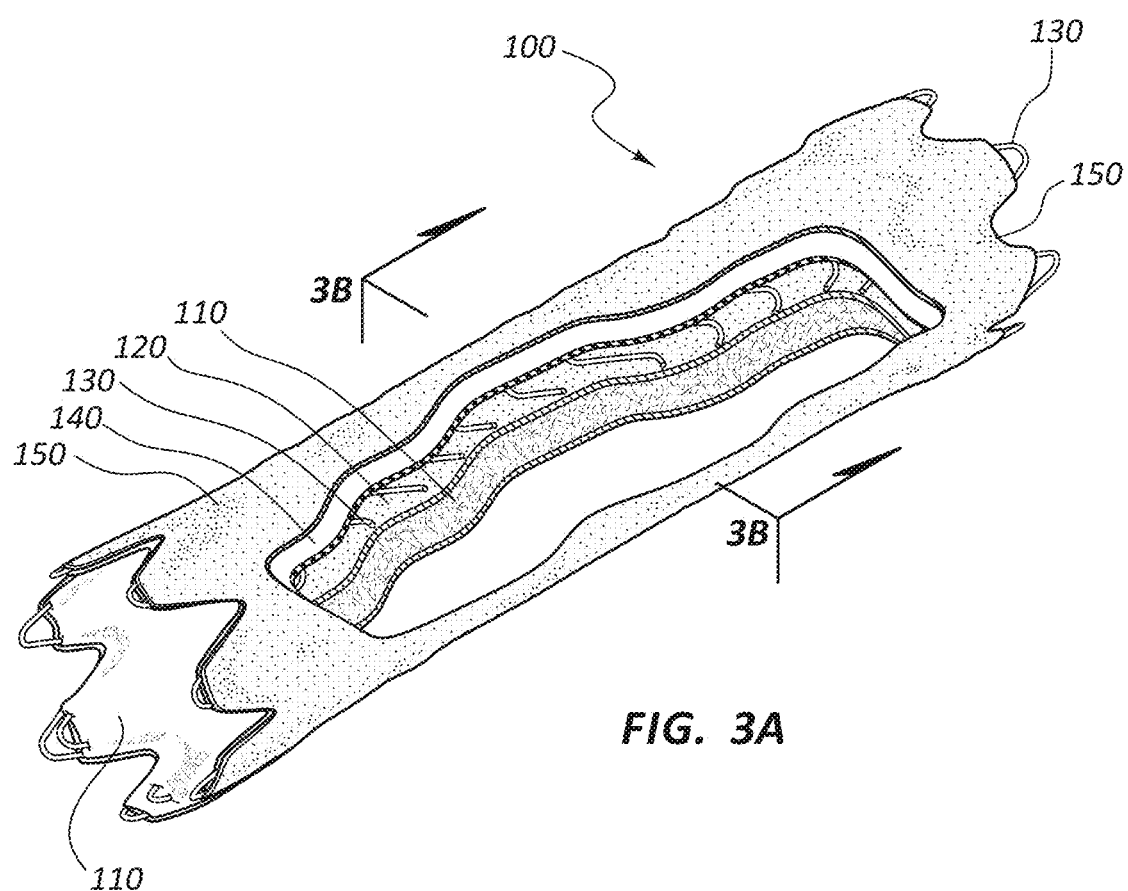
FIG. 3A is a perspective cut-away view of a medical appliance.
Figure 3B:
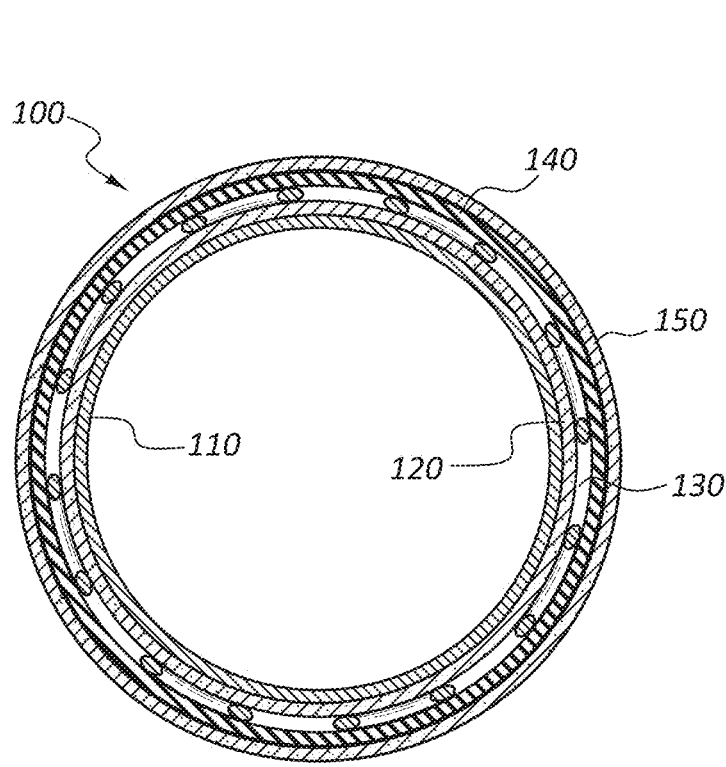
FIG. 3B is a cross-sectional view of the medical appliance of FIG. 3A taken through line 3B-3B.
Figure 3C:
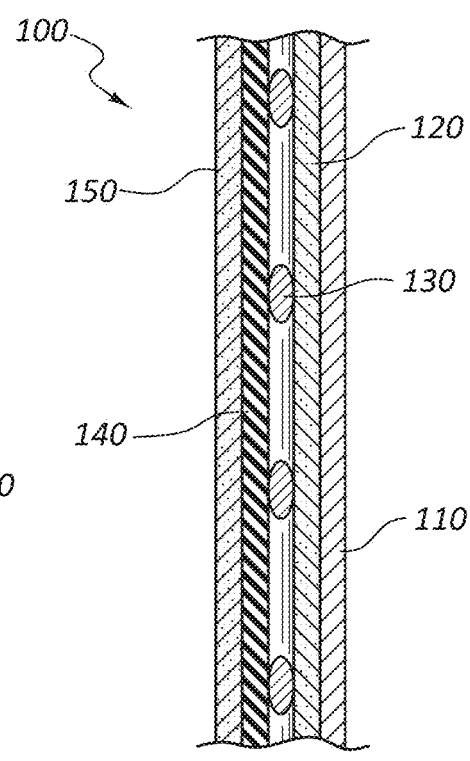
FIG. 3C is a cross-sectional view showing the layers of the medical appliance of FIG. 3A.

FIGS. 3A-3C are schematic depictions of an exemplary medical appliance 100. Specifically, FIG. 3A is a perspective cut-away view of the medical appliance 100. FIG. 3B is a cross-sectional view of the medical appliance 100 taken through line 3B-3B of FIG. 3A. FIG. 3C is another cross-sectional view showing the layers of the medical appliance 100.

The medical appliance 100 of FIGS. 3A-3C may be configured as a vascular stent-graft. In the illustrated embodiment, the medical appliance 100 is shown with four distinct layers disposed about a scaffolding structure 130. In the illustrated embodiment, the medical appliance comprises a first layer 110 of rotationally spun PTFE. The rotationally spun PTFE first layer 110 defines the luminal surface of the medical appliance 100. This luminal first layer 110 may be designed to interact with blood flow within the vasculature. For example, the microporous structure of the rotationally spun first layer 110 may be configured to accommodate or allow endothelial cell growth on the luminal surface of the medical appliance 100 when disposed within the vasculature of a patient. Alternatively or additionally, it is within the scope of this disclosure to use any serially deposited material on the luminal surface of the medical appliance 100. For example, rotational spun PTFE, electrospun PTFE, or other polymers may be used on this layer.

Serially deposited layers within the scope of this disclosure may comprise a wide variety of characteristics. For example, serially deposited layers with a percent porosity between 35% and 75%, including between 40% and 60%, and between 45% and 55%, are within the scope of this disclosure. Similarly, serially deposited layers with an average fiber diameter between 0.25 micron and 2.5 micron, including between 0.5 micron and 1.75 micron, and between 0.75 micron and 1.25 micron, are within the scope of this disclosure. Average pore diameter for serially deposited layers within the scope of this disclosure may range from one micron to five micron, including from two micron to four micron and from two micron to three micron. Finally, the average pore area of serially deposited layers within the scope of this disclosure may range from three square micron to 15 square micron, including from four square micron to 10 square micron, and from four square micron to eight square micron. Any serially deposited layer forming a portion of a construct described herein may be configured with any of these properties.

In the illustrated embodiment, the medical appliance 100 comprises a second layer 120 disposed radially around the first layer 110. The second layer 120 may be configured to reinforce or otherwise strengthen the first layer 110 of rotational spun material. In some embodiments, this second layer 120 may comprise ePTFE. The ePTFE layer may reinforce the rotational spun first layer 110. For example, the ePTFE layer may increase the tensile strength, burst strength, hoop strength, or other properties of the medical appliance 100 as compared to a device utilizing only serially deposited fibers.

In some embodiments, the ePTFE may comprise densified ePTFE and/or ePTFE with a small IND. The ePTFE second layer 120 may be configured with low porosity and high work history to create a high-strength layer.

ePTFE layers within the scope of this disclosure may be configured with a variety of properties. For example, ePTFE layers with an average internodal distance (IND) of less than 80 micron, including less than 70 micron, less than 60 micron, less than 50 micron, less than 40 micron, less than 30 micron, less than 20 micron, and less than 10 micron, are within the scope of this disclosure. Additionally, exemplary ePTFE layers within the scope of this disclosure may have an average IND of less than 10, nine, eight, seven, six, five, four, three, two, or one micron.

Additionally, ePTFE layers within the scope of this disclosure may have percent porosities between 40% and 80%, including percent porosities greater than 50%. Further, such layers may have an average pore diameter greater than 1 micron, including between one micron and three micron. Average pore area may be greater than two square micron, including between two square micron and 15 square micron. Finally, the average fibril diameter of the ePTFE layer may be greater than 0.2 micron, including between 0.2 micron and 0.6 micron.

One exemplary ePTFE layer may have an IND of 10 micron, a percent porosity of 75%, average pore diameter of 4.38 micron, average pore area of 14.7 square micron, and average fibril thickness of 0.33 micron. A second exemplary ePTFE layer may have an IND of 10 micron, a percent porosity of 65%, average pore diameter of 3.5 micron, average pore area of 10.6 square micron, and average fibril thickness of 0.35 micron. A third exemplary ePTFE layer may have an IND of 10 micron, a percent porosity of 50%, average pore diameter of 2.78 micron, average pore area of 7.5 square micron, and average fibril thickness of 0.5 micron.

ePTFE layers according to the three exemplary layers above, as well as ePTFE layers within any of the ranges disclosed herein, may be used in multilayered constructs within the scope of this disclosure.

As compared to serially deposited layers, ePTFE layers may have a greater tensile strength, creep resistance, or other mechanical properties. For example, a multilayered construct may be comprised of both serially deposited layers and ePTFE layers wherein at least one ePTFE layer has five to 10 times greater tensile strength than at least one serially deposited layer within the same construct.

Multilayered coverings or constructs wherein one or more layers of ePTFE provide at least 90% of at least one mechanical property (such as tensile strength, hoop strength, burst strength, and/or creep resistance) of the covering or construct are within the scope of this disclosure. In some instances such a construct may have no scaffolding structure. In other embodiments, the comparison of properties may only refer to the properties provided by the covering portion, meaning the layers of material disposed about a scaffolding structure, but not including the scaffolding structure. Still further, this comparison of properties may refer to the properties of the entire construct, including a scaffolding structure. Furthermore, coverings or constructs wherein at least 85%, 80%, 75%, 70%, and 65% of at least one mechanical property is provided by one or more layers of ePTFE are within the scope of this disclosure.

In the illustrated embodiment, the scaffolding structure 130 is disposed around the second layer 120 of the medical appliance 100. This scaffolding structure 130 may comprise a metal stent—for example, a stent composed of nitinol, stainless steel, or alloys thereof. Additionally, other materials, such as polymer scaffolds, are within the scope of this disclosure. In some embodiments, the scaffolding structure 130 may be understood as a third layer of the medical appliance 100. For example, as the scaffolding structure 130 may be disposed between other such layers (such as the second layer 120 and the fourth layer 140) is can be understood as representing a layer of the medical device 100. Still further, in some embodiments the scaffolding structure may comprise a relative tight lattice, including a polymer lattice, which may tend to form a layer of a medical appliance 100. References herein to a multilayered construct or multilayered component may be understood as referring to the entire medical appliance 100, including the scaffolding structure, or may apply only to layers of material (such as 110, 120, 140, and 150) disposed about a scaffolding structure 130 considered separately from the scaffolding structure 130.

The medical appliance 100 may further comprise an impermeable layer. For example, in the illustrated embodiment, the fourth layer 140 may comprise a polymer layer that is impermeable to cellular growth, fluid passage, or both. An impermeable layer may be configured to prevent fluid leakage across the medical appliance and/or prevent cellular growth across the appliance. Containment of cellular growth across the appliance may lengthen the useful life of the appliance, as bodily tissues are prevented from growing through the medical appliance and occluding the lumen thereof.

In some embodiments, the impermeable fourth layer 140 may comprise fluorinated ethylene propylene (FEP) that may be sprayed, dipped, or laminated onto the construct. FEP layers within the scope of this disclosure may thus be applied as a film or membrane which is rolled onto or otherwise applied to a construct, as well as applied as a liquid or solution applied by spraying or dipping.

The medical appliance 100 may further comprise a fifth layer 150 disposed around the impermeable fourth layer 140. This fifth layer 150 may define an abluminal surface of the medical appliance 100. In some instances, this fifth layer 150 may comprise ePTFE and may be densified and/or have a relatively small IND or pore size. This layer may be configured to provide strength to the construct and may or may not comprise ePTFE having the same properties as the second layer 120 of the illustrated construct.

In some embodiments, the fourth layer 140 and the fifth layer 150 may be constructed as a composite layer. For instance, a fifth layer 150 comprising ePTFE may be sprayed or dipped with FEP such that the FEP coats the ePTFE and fills in the pores and openings in the ePTFE. A composite layer of ePTFE and FEP may thus be configured with the properties and functions of both the fourth layer 140 and fifth layer 150.

Any of the layers discussed above (110, 120, 140, 150) may be comprised of one or more sublayers. For example, if the first layer 110 is comprised of serially deposited fibers, the first layer 110 may, in turn, comprise multiple sublayers of serially deposited fibers or fiber mats. In an exemplary embodiment, the first layer 110 may thus consist of a first sublayer comprising serially deposited fibers and a second sublayer also comprising serially deposited fibers. The sublayers may be deposited at different times during manufacture and/or may be sintered separately, for example. The first layer 110 may also include other materials, disposed between the sublayers, for example to aid in coupling the sublayers to each other. Any number of sublayers may be combined within a single layer.

In some embodiments, the wall thickness of a multilayered covering for a medical device may be between 50 micron and 500 micron, including between 50 micron and 450 micron, between 50 micron and 400 micron, between 50 micron and 350 micron, between 50 micron and 300 micron, between 50 micron and 250 micron, between 50 micron and 200 micron, between 50 micron and 150 micron, and between 75 micron and 125 micron.

The wall thickness of any individual layer within a multilayered construct may be between five micron and 100 micron, including between five micron and 75 micron, between five micron and 60 micron, between 25 micron and 75 micron, between 10 micron and 30 micron, and between five micron and 15 micron. Any layer described herein may fall within any of these ranges, and the thicknesses of each layer of a multilayered construct may be configured such that the total wall thickness of the covering falls within the ranges described above.

Multilayered constructs that have more or fewer layers than the exemplary medical appliance 100 are likewise within the scope of this disclosure. For example, constructs having two, three, four, five, six, seven, or more layers are all within the scope of this disclosure. In some embodiments, a single layer may be used to provide the characteristics associated with two or more layers in the exemplary medical appliance 100. For example, ePTFE with a sufficiently small IND may be substantially impermeable to tissue ingrowth and/or fluid passage. Therefore, in some embodiments, a single layer of low-porosity ePTFE may provide the characteristics associated with the second 120, fourth 140, and fifth 150 layers of the exemplary medical appliance 100. A medical appliance comprising a single luminal layer of serially deposited fibers and a single layer of ePTFE is within the scope of this disclosure.

Further, the order of the layers may be varied. For example, any of the layers described in connection with the exemplary medical appliance 100 may be disposed in any relative order, with the exception that a layer configured as a blood-contacting layer of the device (if present) will be disposed on the luminal surface of the construct.

Furthermore, medical appliances within the scope of this disclosure may be manufactured in a variety of ways. Each layer may be individually formed then disposed on the construct, or one or more layers may be formed on the construct in the first instance.

With reference to the medical appliance 100 of FIGS. 3A-3C, a method of manufacture may comprise serially depositing PTFE fibers on a mandrel or other collection surface and sintering the fibers. This layer of serially deposited fibers may form the first layer 110 of the medical appliance 100.

A second layer 120 may then be applied to the medical appliance 100. This second layer 120 may comprise ePTFE and may be densified. In some embodiments, the ePTFE may be obtained as a sheet which is applied around the first layer 110.

Additionally, in some embodiments the second layer 120 may be applied around the first layer 110 before the first layer 110 is sintered. Sintering of the first layer 110 while the second layer 120 is disposed therearound may facilitate bonding between the first 110 and second 120 layers. Similarly, in some embodiments, the second layer 120 may be applied as unsintered ePTFE around the first layer 110, which in turn may comprise unsintered serially deposited PTFE fibers. Accordingly, the first 110 and second 120 layers may be simultaneously sintered, which may facilitate bonding between the layers. Any layer of PTFE, including serially deposited layers and layers of ePTFE, may be applied as an unsintered layer.

In some embodiments, the mechanical properties of an ePTFE layer may be derived from the relative disposition of ePTFE sublayers which comprise the overall ePTFE layer. Each sublayer may impart different properties to the overall construct. For example, the sublayers may be stronger in the direction the ePTFE was expanded than in a transverse direction. Application of such sublayers such that the axis of expansion of each sublayer is perpendicular to the axis of expansion of adjacent layers may create a layer of ePTFE with more uniform longitudinal and radial properties. Constructs within the scope of this disclosure may comprise ePTFE sublayers disposed such that the axis of expansion of a first layer is disposed at any angle to the axis of expansion of an adjacent layer. Further, constructs wherein the axis of expansion of an ePTFE sublayer is aligned with the central axis of a prosthesis, for example the longitudinal axis of a tubular prosthesis, are within the scope of this disclosure.

In some embodiments this may be done by obtaining a strip of ePTFE that is narrower than the length of the medical appliance 100. The strip may be helically wrapped around the first layer 110 of the medical appliance 100. In some instances the strip may be wrapped at about 45° to the longitudinal axis of the medical appliance 100. The strip may comprise a sublayer of the second layer 120. A second sublayer may be applied, also at about 45° to the longitudinal axis of the medical appliance 100, but applied such that the axis of expansion of the second sublayer is perpendicular to the first strip applied. The combined strength of the sublayers may thus be arranged such that the sum of the strength of the sublayers is similar in the longitudinal and radial directions of the medical appliance 100. Any other angle of relative positioning of sublayers is within the scope of this disclosure, and the relative angles may be configured to create a construct with certain properties and strengths in various directions.

A metal or polymer scaffolding structure 130 may then be applied around the second layer 120 of the medical appliance 100. The fourth layer 140 may then be applied. The fourth layer 140 may comprise FEP and may be applied as a film, dipped, sprayed, or otherwise applied. Finally, the fifth layer 150 may be applied around the fourth layer 140. The fifth layer 150 may or may not be applied in the same manner as the second layer 120 and may or may not have substantially the same properties as the second layer 120.

In embodiments wherein the fifth layer 150 comprises PTFE, including ePTFE, the fifth layer 150 may or may not be sintered at the same time as other layers, for example, the second layer 120. In some embodiments, the first 110 and second 120 layers may first be applied and sintered (either separately or simultaneously), the scaffolding structure 130 may then be applied, followed by the fourth layer 140. In some embodiments, the fourth layer 140 may comprise FEP and may be applied as a film or as a liquid or solution. In embodiments wherein the fourth layer 140 is FEP and the fifth layer PTFE, such as ePTFE, the fifth layer 150 may be sintered after it is applied around the fourth layer 140. In some such embodiments, a film FEP fourth layer 140 may bond to adjacent layers during the heating of the construct to sinter the fifth layer 150. Again the first 110 and second 120 layers may be previously sintered.

Methods of deploying a medical appliance, such as medical appliance 100, within the body are also within the scope of this disclosure. Similarly, methods of promoting endothelial growth while resisting transmural tissue growth across the medical appliance are within the scope of this disclosure. For example, deployment of a medical appliance having a blood-contacting layer configured to promote endothelial growth and at least one other layer configured to resist tissue growth through the layer would be related to such a method.

Figure 4:
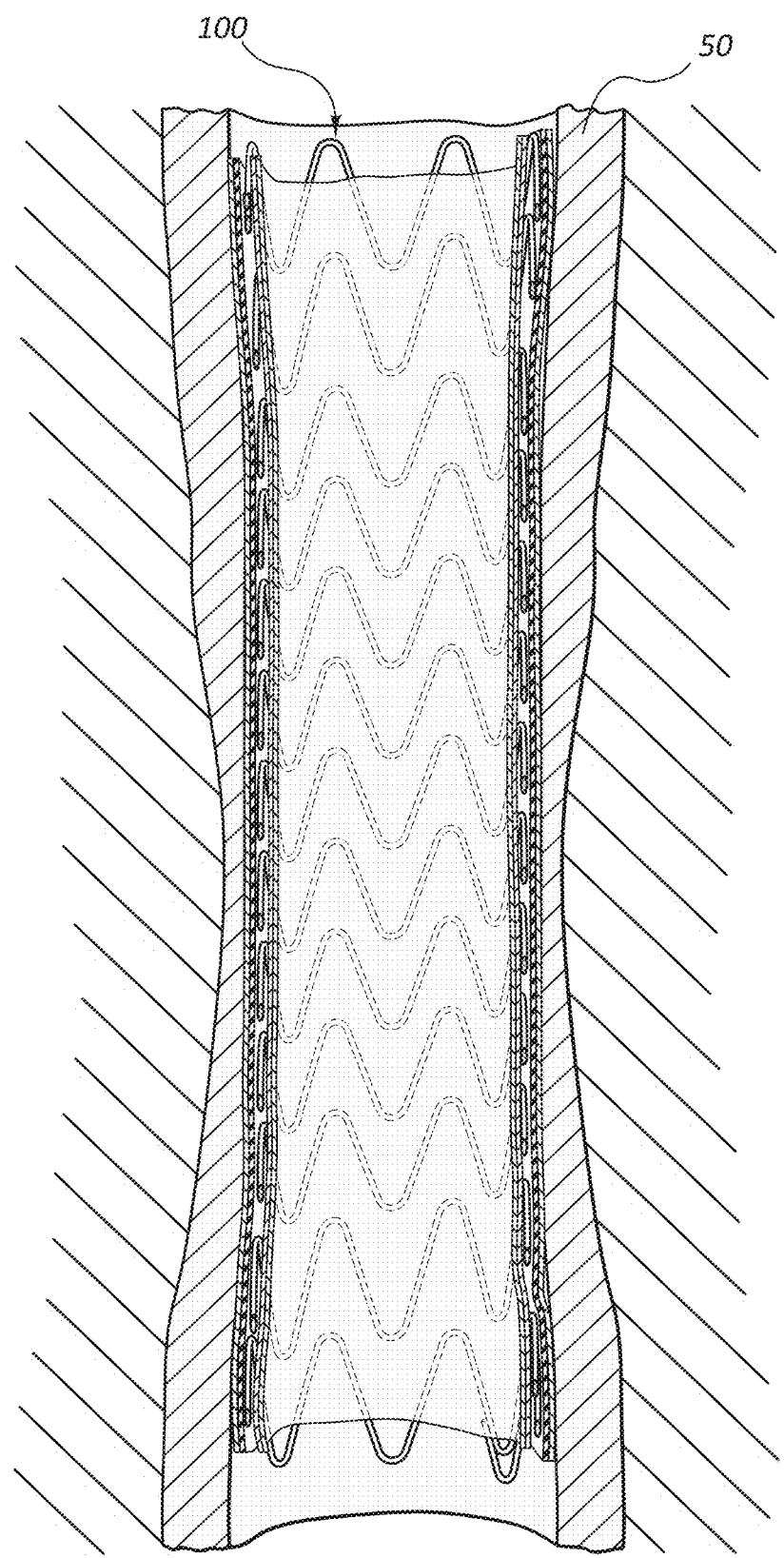
FIG. 4 is a cross-sectional schematic view of the medical appliance of FIG. 3A deployed within a body lumen.

FIG. 4 is a cross-sectional schematic view of the medical appliance 100 deployed within a body lumen 50. As shown, when the medical appliance 100 is so deployed, the fifth layer (150 of FIG. 3A), which may comprise an abluminal surface of the medical appliance 100, may be disposed in direct contact with the wall of the body lumen 50. The first layer (110 of FIG. 3A), which may comprise a luminal surface of the medical appliance 100, may be disposed in direct communication with fluid flowing through the body lumen 50. Characteristics of the various other layers of the medical appliance 100 may also affect the interaction between the body lumen 50 and the medical appliance 100, though these layers may not be in direct contact with a surface of the body lumen 50. For example, a cellular or fluid impermeable layer may prevent tissue or fluid from crossing the wall of the medical appliance 100, though such a layer may or may not be disposed in direct contact with the body lumen 50.

Figure 5:
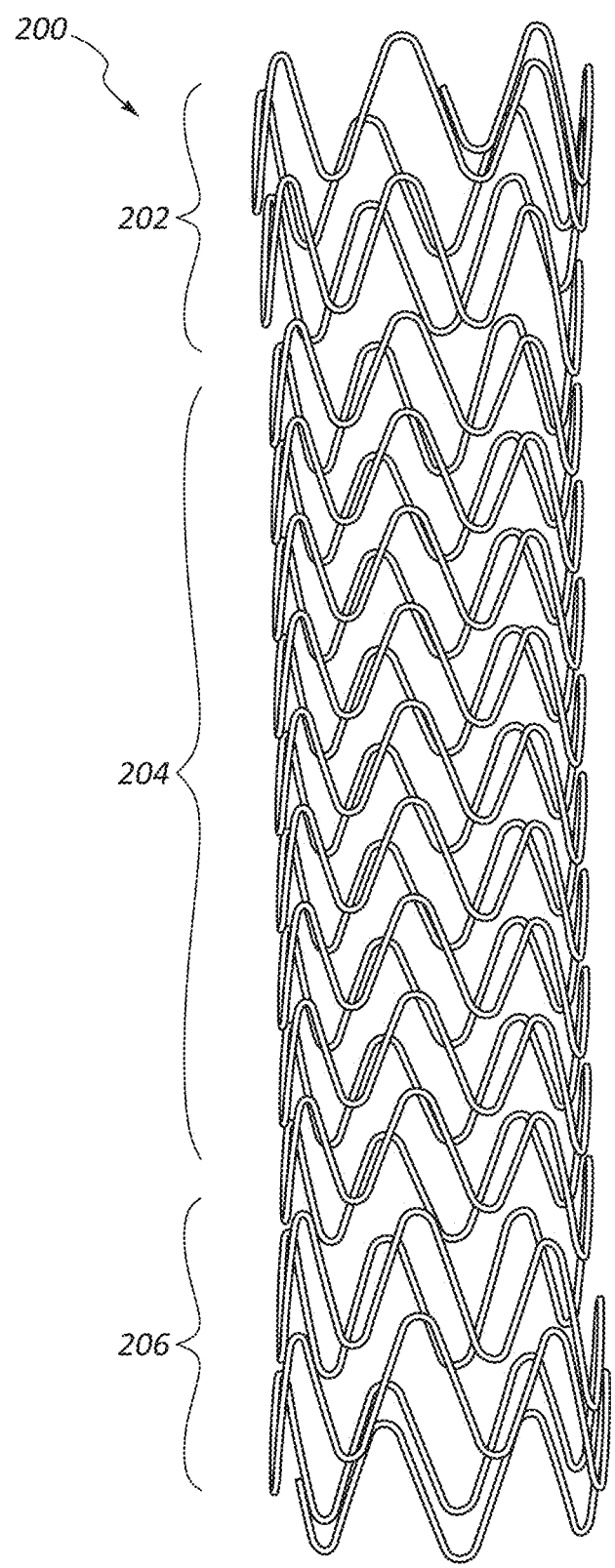
FIG. 5 is a perspective view of a scaffolding structure for a stent-graft.

FIG. 5 is a perspective view of a scaffolding structure 200 for a stent-graft. Such scaffolding structures may be coupled to coverings, including layered coverings, and may be configured to provide support and structure to the stent-graft. For example, a scaffolding structure, such as scaffolding structure 200, may be configured to resist radial compression of a stent-graft. Though references below may be directed to the scaffolding structure 200, it will be understood, by one having skill in the art and having the benefit of this disclosure, that disclosure relevant to the scaffolding structure 200 may analogously apply to a stent-graft or covered stent composed of the scaffolding structure 200.

In some embodiments, the scaffolding structure 200 may be configured with different resistance to radial force along the longitudinal length of the scaffolding structure 200. For example, in the illustrated embodiment, the scaffolding structure 200 comprises a proximal portion 202, a mid-body portion 204, and a distal portion 206. The scaffolding structure 200 may be configured such that it provides greater resistance to radial compression in one or more of these portions 202, 204, 206 as compared to at least one other portion 202, 204, 206 of the scaffolding structure 200. Differing resistance to radial force along the length of the scaffolding structure 200 may be designed to provide strength in certain areas (such as an area to be treated, such as an aneurysm) while providing softer portions of the scaffolding which may allow the scaffolding structure 200 to interact with healthy portions of the body in a more atraumatic way. Thus one or more portions of a scaffolding structure may be configured to hold open diseased tissue within the body lumen 50.

The radial resistance of the scaffolding structure 200, and any stent-graft comprising the scaffolding structure 200, may be a result of the material used to create the scaffolding structure 200; variations in the structure of the scaffolding structure 200, such as the degree to which the scaffolding structure 200 comprises a more open or more closed design; and other design parameters. In some embodiments within the scope of this disclosure, the radial force along portions of the same scaffolding structure, stent, or stent-graft may vary by between 10% and 30%, between 30% and 60%, between 60% and 100%, more than 100%, and more than 200%.

In some embodiments, the scaffolding structure 200 may be configured such that the resistance to radial compression of the scaffolding structure 200 is greater in the mid-body portion 204 of the scaffolding structure 200 as compared to the proximal 202 and/or distal 206 portions thereof. In other embodiments the mid-body portion 204 may have less resistance to radial compression or, in other words, may be softer than the proximal 202 and/or distal 206 portions thereof. Still further, in some embodiments the proximal 202 and/or distal 206 portions of a scaffolding structure 200 may be configured to reduce tissue aggravation at the edge of the scaffolding structure 200. In some instances the resistance to radial compression of one or more ends of the scaffolding structure 200 may be configured to reduce the occurrence of edge stenosis. Moreover, the resistance to radial compression of one or more ends of the scaffolding structure 200 may be configured to promote endothelial cell growth on a surface of a stent-graft coupled to the scaffolding structure 200. The resistance to radial compression along one or more portions of the scaffolding structure 200 may be configured to match the compliance of a body vessel in which the scaffolding structure 200 is designed for deployment.

Scaffolding structures 200 may comprise metals, including stainless steel, nitinol, various super elastic or shape memory alloys, and so forth. Scaffolding structures 200 may also comprise polymers. Further, scaffolding structures 200 may comprise one or more biologic agents, including embodiments wherein a metal or polymeric scaffolding structure is integrated with a drug or other biologic agent.

Scaffolding structures 200 may be formed in a variety of ways. In some embodiments, the scaffolding structure 200 may be formed of a wire. Further, the scaffolding structure 200 may be formed from a tube of material, including embodiments wherein the scaffolding structure 200 is cut from a tube of material. Scaffolding structures 200 may be formed using laser cutting, etching processes, and powdered metallurgy and sintering processes; formed from molds; and formed using rapid manufacturing techniques.

A stent or stent-graft, with or without a scaffolding structure such as scaffolding structure 200, may be configured to exert an outward radial force when disposed within a body lumen. This force may be configured to keep the lumen open, prevent restenosis, inhibit migration of the stent or stent-graft, and so forth. However, stents or stent-grafts which subject body lumens to high radial forces may provoke an unwanted biologic response and/or result in unnecessary trauma to the body lumen. Accordingly, a stent or stent-graft may be configured to exert radial force within a range that is acceptable for healing and trauma, while still achieving treatment goals.

Some stents or stent-grafts may be configured such that the stent or stent-graft resists localized compression, for example due to a point or pinch force, even when the localized force exceeds the circumferential outward radial force of the stent or stent-graft. In other words, the stent may be configured to resist relatively high point forces (for example, as may be exerted by a ligament or other biologic structure) on the stent or stent-graft without exerting high radial forces on the entire body lumen.

Stents or stent-grafts within the scope of this disclosure may be configured such that the point force required to fully collapse the stent is between five N and 15 N, including between 7.5 N and 12.5 N. Stents or stent-grafts within the point force ranges disclosed above may have a lower circumferential radial outward force. For example, stents or stent-grafts within the scope of this disclosure may have a radial outward force at 20% oversizing of between 0.3 N/mm and 1.3 N/mm, including between 0.4 N/mm and 1 N/mm. Thus, the point force required to fully collapse the stent may be significantly greater than the radial outward force exerted by the stent on a body lumen.

Multilayered stent covers within the scope of this disclosure may be tested by pressurizing water within the lumen of a stent according to the present disclosure. By increasing the water pressure, the burst strength and water permeability of the stent can be determined. Water entry pressure is herein defined as the internal water pressure at which a second bead of water forms on the outside of the tubular structure being tested. The device does not burst or fail in the water entry pressure test. Medical devices within the scope of this disclosure may have water entry pressures between zero psi and 10 psi, including between four psi and eight psi. Furthermore, medical devices within the scope of this disclosure may have water entry pressures greater than five psi, greater than 10 psi, greater than 20 psi, greater than 30 psi, greater than 40 psi, or greater than 50 psi.

The examples and embodiments disclosed herein are to be construed as merely illustrative and exemplary, and not as a limitation of the scope of the present disclosure in any way. It will be apparent to those having skill in the art with the aid of the present disclosure that changes may be made to the details of the above-described embodiments without departing from the underlying principles of the disclosure herein. It is intended that the scope of the invention be defined by the claims appended hereto and their equivalents.

The invention claimed is:

1. A multilayered vascular prosthesis, comprising:
a luminal surface comprising a serially deposited fiber layer; and
an expanded polytetrafluoroethylene (ePTFE) layer coupled to the serially deposited fiber layer, wherein,
the ePTFE layer comprises one or more sublayers of ePTFE, and
an axis of longitudinal expansion of at least one of the ePTFE sublayers is disposed at an angle to an axis of longitudinal expansion of at least one adjacent ePTFE sublayer;
wherein at least one of the ePTFE sublayers is configured to be impermeable to red blood cell migration; and
wherein the one or more sublayers of ePTFE comprise different average pore sizes.

2. The multilayered vascular prosthesis of claim 1, wherein the axis of longitudinal expansion of at least one of the ePTFE sublayers is disposed at an angle between 0 degrees and 90 degrees to the axis of longitudinal expansion of at least one adjacent ePTFE sublayer.

3. The multilayered vascular prosthesis of claim 1, wherein the axis of longitudinal expansion of at least one of the ePTFE sublayers is perpendicular to the axis of longitudinal expansion of at least one adjacent ePTFE sublayer.

4. The multilayered vascular prosthesis of claim 1, wherein the axis of longitudinal expansion of at least one of the ePTFE sublayers is at an angle to a longitudinal axis of the multilayered vascular prosthesis.

5. The multilayered vascular prosthesis of claim 1, wherein an average pore size of at least one of the ePTFE sublayers is different than an average pore size of at least one adjacent ePTFE sublayer.

6. The multilayered vascular prosthesis of claim 1, wherein pores of at least one of the ePTFE sublayers are misaligned with pores of at least one adjacent ePTFE sublayer such that a tortuous path is defined between the pores of the sublayers.

7. The multilayered vascular prosthesis of claim 1, wherein at least one of the ePTFE sublayers is coupled to a non-porous layer.

8. A multilayered vascular prosthesis, comprising:
a luminal surface comprising a serially deposited fiber layer; and
an expanded polytetrafluoroethylene (ePTFE) layer coupled to the serially deposited fiber layer, the ePTFE layer providing at least 65% of the tensile strength, measured in at least one direction, of a construct consisting of the serially deposited fiber layer and the ePTFE layer;
wherein the ePTFE layer comprises two or more sublayers of ePTFE,
wherein the ePTFE layer is configured to be impermeable to red blood cell migration across the ePTFE layer, and
wherein pores of at least one of the ePTFE sublayers are misaligned with pores of at least one adjacent ePTFE sublayer.

9. The multilayered vascular prosthesis of claim 8, wherein an average pore size of at least one of the ePTFE sublayers is different than an average pore size of at least one adjacent ePTFE sublayer.

10. The multilayered vascular prosthesis of claim 8, wherein at least one of the ePTFE sublayers is coupled to a non-porous layer.

11. The multilayered vascular prosthesis of claim 8, wherein an axis of longitudinal expansion of at least one of the ePTFE sublayers is disposed at an angle to an axis of longitudinal expansion of at least one adjacent ePTFE sublayer.

12. The multilayered vascular prosthesis of claim 11, wherein the axis of longitudinal expansion of at least one of the ePTFE sublayers is disposed at an angle between 0 degrees and 90 degrees to the axis of longitudinal expansion of at least one adjacent ePTFE sublayer.

13. The multilayered vascular prosthesis of claim 11, wherein the axis of longitudinal expansion of at least one of the ePTFE sublayers is disposed at an angle to a longitudinal axis of the multilayered vascular prosthesis.

* * * * *